United States Patent [19]

Wagner et al.

[11] Patent Number: 5,481,043
[45] Date of Patent: Jan. 2, 1996

[54] PHENONE COMPOUNDS, MANUFACTURING METHOD AND PHARMACEUTICAL PREPARATIONS CONTAINING THEM

[75] Inventors: Hildebert Wagner, Breitbrunn am Chiemsee; Walter Dorsch, München, both of Germany; Hermann Stuppner, Innsbruck, Austria; Sandor Antus, Budapest, Hungary

[73] Assignee: Plantamed Arzneimittel GmbH, Neumarkt/OPF, Germany

[21] Appl. No.: 838,156

[22] Filed: Feb. 18, 1992

[30] Foreign Application Priority Data

Feb. 26, 1991 [DE] Germany ............... 41 06 028.8
Jan. 24, 1992 [DE] Germany ............... 42 01 942.7

[51] Int. Cl.⁶ ............... C07H 15/203; C07C 47/575; A61K 31/70
[52] U.S. Cl. ............... 568/309; 568/312; 568/316; 568/323; 568/335; 536/4.1
[58] Field of Search ............... 536/4.1; 514/25, 514/688, 689, 826; 568/309, 312, 316, 323, 335

[56] References Cited

U.S. PATENT DOCUMENTS 4,945,099  7/1990  Bollinger et al. ............... 514/381

OTHER PUBLICATIONS

*Chemical Abstracts,* vol. 105, (1986); p. 370.
Patent Abstracts of Japan, C–696, Mar. 5, 1990, vol. 14/No. 115.
Budavari, Susan, Ed., *the Merck Index,* 11th Ed., Merck & Co., Inc., Rahway, N.J., (1989): p. 7367.
Delay et al., "New Synthesis of Plant Aryl Glycosides as Potential Gene Inducers", *Carbohydrate Research,* 198 (1990), 223–231.

*Primary Examiner*—Ronald W. Griffin
*Attorney, Agent, or Firm*—Cohen, Pontani, Lieberman, Pavane

[57] ABSTRACT

Certain new phenone derivatives of the formula (I)

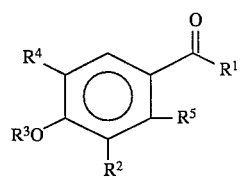

in which
$R^1 = CH_3$,
$R^2 = H$, Cl, Br, I, methyl, hydroxy, methoxy, propoxy, propoxy or ethoxy;
$R^3 = H$ or β-D-glykosyl;
$R^4 = H$, Cl, Br, I, methyl, hydroxy, methoxy, propoxy, isopropoxy or ethoxy;
$R^5 = H$ or hydroxy,
and the pharmaceutically acceptable salts, ethers and esters thereof, with the exception of the compounds 4-hydroxyacetophenone, 4-hydroxy-3-methoxy-acetophenone, 4-glucopyranosyloxy-acetophenone, 4-glucopyranosyloxy-3-methoxyacetophenone, 4-galactopyranosyloxy-3-methoxyacetophenone, 4-glucopyranosyloxy-3,5-dimethoxyacetophenone and galactopyranosyloxy-3,5-dimethoxyacetophenone and a method for manufacturing them and pharmaceutical preparations containing them. The invention also concerns pharmaceutical preparations containing at least one compound of the formula (II)

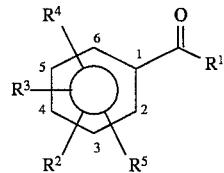

in which
$R^1$ denotes H, OH, alkoxy or $C_{1-8}$ alkyl;
$R^2$ denotes H or $C_{1-4}$ alkoxy;
$R^3$ denotes OH or a β-D/alpha-L-glykosyl group (di-or-triglykosyl) which is substituted optionally by low molecular $C_{1-4}$ aliphatic or aromatic acids,
$R^4$ denotes H or $C_{1-3}$ alkyl or $C_{1-4}$ alkoxy;
$R^5$ denotes H, Cl, Br or I, R being, when it denotes halogen, in ortho position to a OH group,
and the pharmaceutically acceptable salts, ethers and esters thereof together with pharmaceutically acceptable carriers and diluents.

The new compounds including the compounds already known, have an antiphlogistic action. In vivo they inhibit in particular allergen- and PAF-induced bronchial asthma.

9 Claims, 2 Drawing Sheets

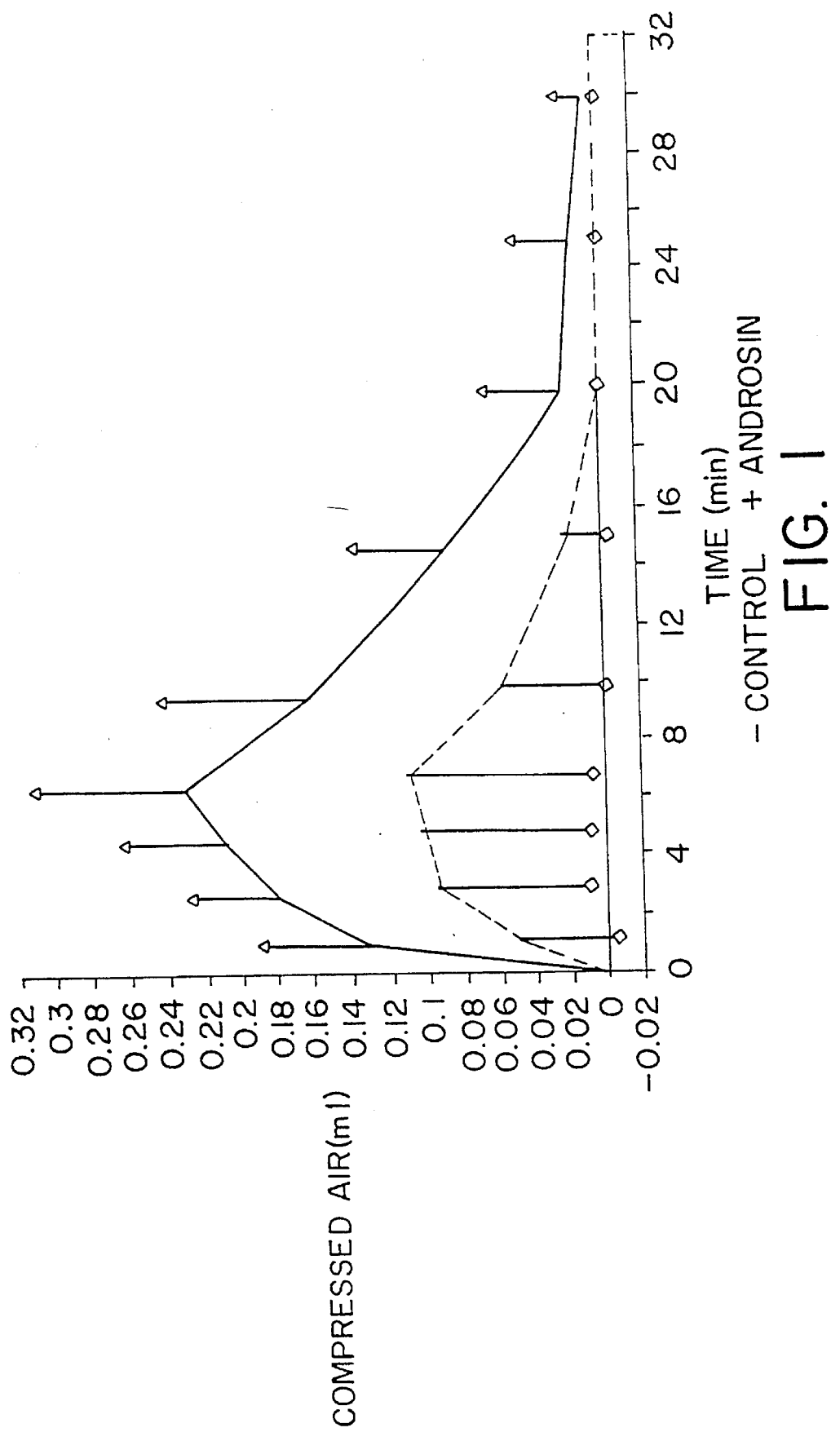

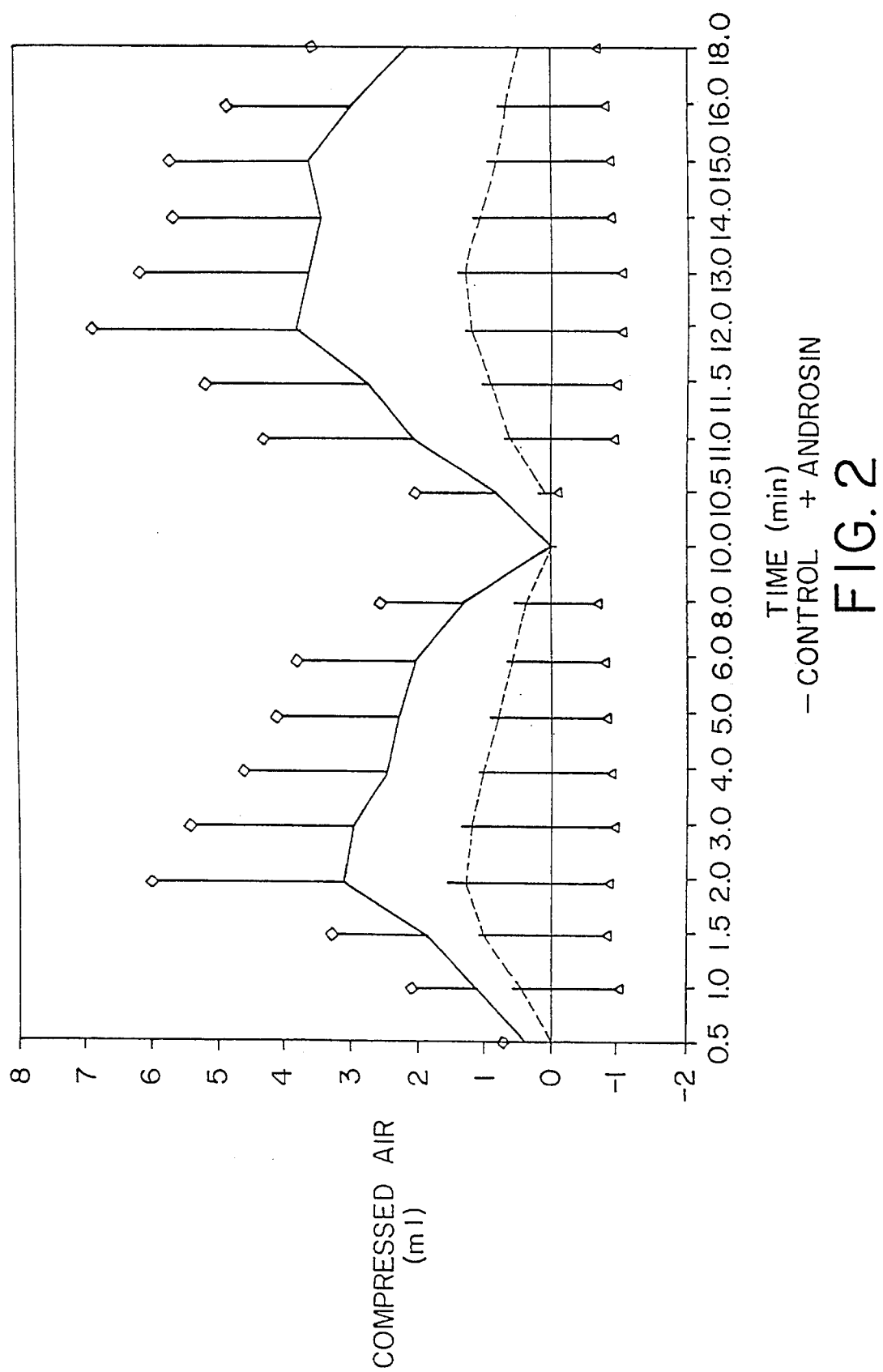

PHENONE COMPOUNDS, MANUFACTURING METHOD AND PHARMACEUTICAL PREPARATIONS CONTAINING THEM

FIELD OF THE INVENTION

The invention concerns certain new phenone compounds, a method for manufacturing them, and pharmaceutical preparations containing them or phenone compounds known per se. The pharmaceutical preparations are for the prophylaxis and therapy of inflammatory diseases of all organs (lungs, liver, etc.), of rheumatic diseases, immunological and allergic diseases, asthmatic diseases and inflammation. The range of application corresponds to that of the most effective antiphlogistic agents to date, namely the corticoids.

BACKGROUND OF THE INVENTION

The term inflammation, as it is to be understood here, is generally understood as a reaction of the organism and its tissues to various harmful stimuli. Harmful stimuli are exogenic and endogenic stimuli, such as for instance tissue injuries, penetration by foreign bodies, chemical substances, bacterial toxins, allergens, immune complexes, microorganisms, pathological metabolic products and decomposition products of tumors. The classical symptoms, pain and fever, are closely related to the inflammation process.

It has been known for a long time that certain substances produced by the body, the so-called mediators, are closely related to the inflammation process. These mediators, which are of extremely great pathogenetic importance, are released from the body's cells by the harmful event (noxe). The most important and best-known mediators are considered to be histamine, 5-HT (5-hydroxytryptamine), bradykinin, the prostaglandins, the prostacyclins, the leukotrienes, thromboxanes and the only recently characterized platelet activating factor (PAF).

These and other mediators, which are not specified individually in detail, have an extremely great effect on the contraction of the smooth muscle, they lead to disorders of cardiac function and impair the integrity of the blood vessels and mucous membranes, such as, for example, those of the bronchial system. They also cause the aggregation of platelets and polymorphonuclear leukocytes with the severe effects of anaphylactic constriction of the airways, blood pressure reduction, cardiac arrhythmias, plasm exudation, tissue edema, hemoconcentration, thrombocytopenia, leukocytopenia, clumping of platelets and polymorphonuclear leukocytes in the pulmonary capillaries as well as highly severe respiratory disorders and circulatory collapse.

Owing to their broad pharmacological spectrum of action, their wide distribution in the organism, their formation by numerous physical, chemical, pathological, pathophysiological and pharmacological influences, as well as owing to their involvement in a large number of pathophysiological processes, the mediators and the influencing thereof by means of pharmaceuticals are of utmost medical significance (cf. "The Pharmacological Basis of Therapeutics, ed. Goodman and Gilman. 6th edition, 1980, Macmillan Publishing Company).

PAF appears to enjoy special importance in the pathogenesis of inflammatory and allergic processes.

PAF is a glycerophosphocholine with the chemical name 1-O-alkyl- 2-acetyl-sn-glyceryl-3-phosphorylcholine. This factor is released by a number of cells, such as macrophages, basophilic and neutrophilic granulocytes, and others, when activated. The release of PAF leads thereafter to the pathological conditions described above and probably to a number of other, hitherto not fully understood, pathological symptoms. PAF need not have a direct effect, rather it may develop its effect by stimulating other mediators. Recent studies have shown that PAF plays an important role in particular in causing clinical bronchial asthma and in other pathological conditions of the lungs, e.g. obstructive bronchitis.

In addition to its important role in causing bronchial asthma and in anaphylaxis, PAF is to be considered a highly potent inflammation mediator possessing the pathological effects already described above.

A large number of the mediators named above, including PAF, are released by a membrane-linked phospholipase from phospholipids of the cell membrane, forming arachidonic acid, on the one hand, and a preliminary stage of PAF, on the other.

Two groups of mediators are formed originating from arachidonic acid:
(i) by the enzyme, cyclooxygenase, the prostaglandins including prostacyclin and thromboxane,
(ii) by the enzyme, lipoxygenase, the open chain hydroperoxy and hydroxy acids and, in particular, the leukotrienes.

The preliminary stage of PAF is transferred into the active compound by an acetyltransferase.

Two groups of active substances are pharmacologically important in the treatment of inflammation; these are, on the one hand, the so-called nonsteroidal antiphlogistic agents, that is compounds and derivatives of salicylic acid. Other compounds with a well-known antiphlogistic action are the pyrazolone derivatives, the para-aminophenol derivatives, the indole derivatives (e.g. indomethacin) and the derivatives of propionic acid. The pharmacological action of all these compounds is based on the fact that they can inhibit cyclooxygenase and thus prevent the synthesis of prostaglandins or thromboxanes.

Salicylic acid and its derivatives and the further compounds of the whole class are burdened by a number of severe and highly severe side effects. Prolonged administration of salicylic acid derivatives, for instance, leads to gastric and intestinal ulcers. The relative intolerance of the pyrazolone derivatives, the hepatotoxic effect of the para-aminophenol derivatives, the general intolerance of indomethacin and the ulcerative effect of the propionic acid derivatives are also well-known.

A further severe disadvantage of nonsteroidal antiphlogistic agents is that they enhance, under certain circumstances, the pathological effect of the mediators, as the inhibition of the cyclooxygenase provides more substrate for lipoxygenase and thus for the formation of leukotrienes.

The nonsteroidal antiphlogistic agents are contrasted by the steroidal antiphlogistic agents, that is the corticosteroids and their derivatives. The antiphlogistic action of the corticosteroids is based on their ability to inhibit both phospholipase and lipoxygenase, thus inhibiting the entire arachidonic acid metabolism. The unfortunate side effects are a disadvantage for therapy with corticosteroids, and only the following are to be mentioned as examples: duodenal or ventricular ulcers, myopathy, osteoporosis, mental disorders, increased susceptibilty to infection, subcapsular cataracts and similar.

In addition to the corticosteroids, selective lipoxygenase inhibitors such as benoxaprofen are in use. This class of substances is also burdened with severe side effects, such as fatal exfoliative dermatitis (scalded skin syndrome).

SUMMARY OF THE INVENTION

The inventors have now surprisingly discovered that certain new phenone compounds of the general formula (I) and known phenone compounds of the general formula (II) given below possess an excellent antiphlogistic action.

The subject of the invention are therefore compounds of the general formula (I):

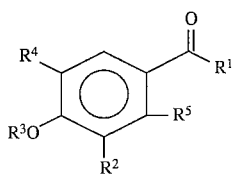

in which
$R^1 = CH_3$,
$R^2 = H$, Cl, Br, I, methyl, hydroxy, methoxy, propoxy, isopropoxy or ethoxy;
$R^3 = H$ or β-D-glykosyl;
$R^4 = H$, Cl, Br, I, methyl, hydroxy, methoxy, propoxy, isopropoxy or ethoxy;
$R^5 = H$ or hydroxy,
and the pharmaceutically acceptable salts, ethers and esters thereof, with the exception of the compounds 4-hydroxyacetophenone, 4-hydroxy-3-methoxy-acetophenone, 4-glucopyranosyloxy-acetophenone, 4-glucopyranosyloxy-3-methoxyacetophenone, 4-galactopyranosyloxy-3-methoxy-acetophenone, 4-glucopyranosyloxy- 3,5-dimethoxyacetophenone and galactopyranosyloxy-3,5-dimethoxy-acetophenone.

The following compounds are preferred:

| $R^1$ | $R^2$ | $R^3$ | $R^4$ |
|---|---|---|---|
| methyl | methyl | β-D-glucosyl | H, Cl, Br or I |
| methyl | H | β-D-glucosyl | H, Cl, Br or I |
| methyl | n-propoxy | β-D-glucosyl | H, Cl, Br or I |
| methyl | isopropoxy | β-D-glucosyl | H, Cl, Br or I |

A further subject of the present invention concerns pharmaceutical preparations containing at least one compound of the above indicated general formula (I) or at least one compound of the following general formula (II):

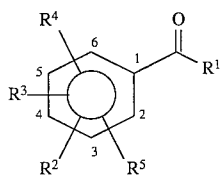

in which
$R^1$ denotes H, OH, alkoxy or $C_{1-8}$ alkyl;
$R^2$ denotes H or $C_{1-4}$ alkoxy;
$R^3$ denotes OH or a β-D/alpha-L-glykosyl group (di-or-triglykosyl) which is substituted optionally by low molecular $C_{1-4}$ aliphatic or aromatic acids,
$R^4$ denotes H or $C_{1-3}$ alkyl or $C_{1-4}$ alkoxy;
$R^5$ denotes H, Cl, Br or I, $R^5$ being, when it denotes halogen, in ortho position to a OH group,
and the pharmaceutically acceptable salts, ethers and esters thereof together with pharmaceutically acceptable carriers and diluents.

Compounds of the formula (II) in which $R^1 = CH_3$, $R^2 = CH_3O$ in the C-3 position, $R^3 = H$ in the C-5 position if C-3 is substituted with $CH_3O$ are preferred.

A particularly preferred compound of the formula (II) is the androsin compound with $R^1 = CH_3$, $R^2 = CH_3O$ in the C-3 position, $R^3 = $β-D-glucosyloxy and $R^4 = H$ in the C-5 position.

Examples for the radicals in the formulae (I) and (II) for alkoxy are: methoxy, ethoxy, n-propoxy, i-propoxy, butoxy, pentoxy, hexoxy, heptoxy or octoxy with a straight chain or branched structure.

Examples of the alkyl radicals are methyl, ethyl, n-propyl, i-propyl, butyl, pentyl, hexyl, heptyl, octyl with a straight chain or branched structure.

Examples of the glycosyl units are glucosyl, galactosyl, rhamnosyl and arabinosyl.

Examples of the substituents at the glycosyl units are cinnamoyl, caffeoyl and benzoyl radicals.

A further subject of the invention is a method for preparing the compounds of the formula (I).

This method comprises the following steps:
i) an acetophenone of the general formula

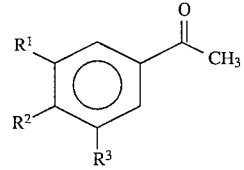

in which
$R^1$ denotes $CH_3O$ or H,
$R^2$ denotes OH,
$R^3$ denotes H, OH or $CH_3O$,
is reacted in alkaline solution with a glucose derivative in an organic solvent;
ii) the reaction mixture is neutralised, the precipitate formed is separated and recrystallized;
iii) the product obtained in ii) is reacted in an alcoholic solution with an alcoholate; and
iv) the reaction mixture is neutralised, the solvent is removed and the residue from $H_2O$ is recrystallized, or for the production of a halogenated acetophenone
   a) an acetophenone of the above general formula is dissolved in a water/methanol mixture,
   b) Na acetate is added and is reacted with a solution of Na-hypochlorite or K-iodide and iod (gaseous) or K-bromide and brom (gaseous) for 1.5 to 3 hours at $-60°$ C. to $90°$ C.,
   c) the reaction product is extracted with chloroform, is washed with Na-thiosulfate and is recrystallized from acetic acid, and it then used for preparing the final compound as mentioned above.

BRIEF DESCRIPTION OF THE FIGURES

FIG. 1 shows the effect of Androsin on PAF inhalation effect; and

FIG. 2 shows the effect of Androsin on ovalbumin inhalation effect.

DETAILED DESCRIPTION OF THE PREFERRED EMBODIMENTS

The compounds and the pharmaceutical preparations according to the invention possess the essential and important property of blocking inflammatory processes of allergic pathogenesis, particularly PAF-induced effects. Therefore, the compounds according to the invention of the formulae (I) and (II) have the property of steroidal antiphlogistic agents but do not display their unfortunate side effects and are therefore valuable for the prophylaxis and treatment of inflammatory processes in the broadest sense in the development of which the well-known mediators, such as prostaglandins, histamine, PAF, leukotrienes and thromboxanes play a role.

In contrast to the non-steroidal antiphlogistic agents, which do not act against the leukocyte-induced effects of chronically inflammatory diseases, as they do not inhibit leukotriene formation, the compounds used here are also superior to the well-known compounds in this respect owing to their surprising, excellent and beneficial action.

The compounds according to the invention fulfil the requirement for non-steroidal antiphlogistic agents which inhibit the synthesis of the leukotrienes and prostaglandins and thromboxanes and counteract the effects of the PAF factor. They are free from the disadvantages connected with the steroidal or non-steroidal antiphlogistic agents.

The pharmaceutical preparations according to the invention have not been shown to have any toxicity to date.

The compounds and their pharmaceutically acceptable preparations can be administered in small doses to obtain a therapeutic, anti-inflammatory effect.

The drugs according to the invention can be used for the treatment of inflammations of the joints, the skin, the mucous membranes and inner organs, irrespective of whether the inflammation was caused by infective agents, immunological processes or traumata. In this context, inflammatory processes of the bronchial system in particular, such as bronchial asthma or obstructive bronchitis, are particularly advantageously treated indications. In addition, the drugs according to the invention can be used for the prophylaxis and treatment of vascular and cardiac diseases in which it appears desirable to inhibit the biosynthesis of inflammatory substances by platelets. The drugs according to the invention can be used to particular advantage for the prophylaxis and treatment of all PAF- and/or leukotriene-induced phenomena and, in particular, for the treatment of the bronchial region.

The necessary quantity of the compound to be used (hereinafter referred to as the active ingredient) in the drug for the desired therapeutic effect depends on the respective compound, the mode of administration, the subject to be treated with it, and the respective illness. A suitable dose of a compound for administration to a mammal suffering from an inflammation, a painful or feverish condition, as described above, is about 0.1 µg to 500 mg of the active ingredient per kilogramme of body weight. In the case of systemic administration the dose may be in the range of 0.5 to 500 mg of the active compound per kilogramme of body weight and the most preferred dose in the range of 0.5 to 50 mg per kilogramme of body weight, e.g. 5 to 25 mg per kilogramme of body weight given several times a day, particularly two or three times a day.

In the case of topical administration, e.g. on the skin or mucous membranes, the suitable dose may be considerably larger; in the case of administration by inhalation the dose may, however, be considerably lower than the systemic dose.

Although it is, in principle, possible to administer the active ingredient alone, it is to be preferred to administer the active ingredient in the form of a pharmaceutical formulation containing a compound in accordance with the general formula and a pharmaceutically acceptable carrier substance for it. Generally, the active ingredient is present in such a formulation in a concentration of 0.1 to 99.9 weight % of the formulation. A single dose of the formulation generally contains between 0.1 mg and 1 g of the active ingredient. For topical administration, the concentration of the active ingredient is preferably 1 to 2 weight % of the preparation, but the active ingredient may account for up to 10 weight %. Preparations intended for nasal or buccal administration, such as, for example, self-atomizing powders, sprays or other well-known and conventional devices, may contain 0.1 to 20 weight %, e.g. 2 weight % of the active ingredient.

The preparations according to the invention for use in both veterinary and human medicine contain the active ingredient together with a pharmaceutically acceptable carrier substance and, if necessary, other therapeutically active ingredients. The carrier substance must be acceptable in the sense that it is compatible with the other ingredients of the formulation and has no disadvantageous effect on the recipient of the formulation.

Suitably, the formulations are available in the form of an oral, ophthalmological, rectal, parentaral (including subcutaneous, intramuscular and intravenous), intraarticular, topical, nasal or buccal dosage form.

The formulations according to the invention are generally available in the form of a single dose and can be manufactured by any well-known method in the field of pharmaceutical technology. Essentially, all the methods contain the step of joining the active ingredient with the carrier substance, if necessary with one or more additional ingredients. As a rule, the formulations are manufactured by even and intensive mixing of the active ingredient with a liquid carrier or a finely distributed solid carrier or both, and then, if necessary, shaping of the product in the desired preparation form.

The formulations according to the invention for oral administration may be available in the form of discrete units, such as, for example, capsules, cachets, tablets or pastilles, with each form containing a certain quantity of the active ingredient. They may also be available in the form of a powder or in the form of a granulate or in the form of a solution or a suspension in an aqueous or nonaqueous liquid, or in the form of an oil-in-water emulsion or a water-in-oil emulsion. The active ingredient may also be available in the form of a bolus, an electuary or a paste.

If the preparations according to the invention are available in the form of a tablet, this can also be manufactured by compressing or casting the active ingredient, if necessary together with one or more additional ingredients. Compressed tablets can also be manufactured by compressing the active ingredient in a free-flowing form, e.g. as a powder or granulate, if necessary mixed with a binding agent, a lubricant, an inert dilution agent, surface active or dispersion medium in a suitable device. Cast tablets can be manufactured by casting a mixture of the active ingredient in powder form and a suitable carrier substance moistened with an inert liquid dilution agent in a suitable device.

The preparations according to the invention for rectal administration may be available in the form of suppositories with the active ingredient contained in a carrier, e.g. made of cacao butter. It may also be available in the form of an enema.

If the formulations according to the invention are intended for parenteral administration they generally contain a sterile aqueous preparation of the active ingredient which is preferably isotonic with the blood of the recipient.

Preparations according to the invention which are suitable for intraarticular administration may be available in the form of a sterile aqueous preparation of the active ingredient with the active ingredient, if necessary, in microcrystalline form, e.g. in the form of an aqueous microcrystalline suspension.

The formulations according to the invention may also be available in the form of a liposomal preparation or in the form of a biodegradable polymer system for administration of the active ingredient.

Formulations according to the invention suitable for topical administration contain liquid or semi-liquid preparations, such as, for example, liniments, lotions, dressings, oil-in-water or water-in-oil emulsions, such as, for example, creams, ointments or pastes, or solutions or suspensions, such as, for example, drops. For instance, the active ingredient for ophthalmological administration may be available in the form of aqueous eye drops, for example in the form of a 0.1 to 1.0% solution.

Formulations according to the invention for administration through the nose or into the buccal cavity or for inhalation are available in the form of a self-atomizing powder or in the form of spray preparations, e.g. as an aerosol. The formulations preferably yield a particle size in the range of 10 to 200 μm after dispersion, for inhalation preferably between 1 and 100 μm.

Formulations according to the invention may contain the active ingredient also in an aqueous or diluted alcoholic solution. The active ingredient can, if necessary, be converted into a fine mist by a spray device and inhaled by the patient.

Pharmaceutical preparations of this type generally contain a flavouring, such as, for example, sodium saccharin and a volatile oil. Also a buffer substance and/or a surface active agent may be contained in such preparations together with preservatives, such as, for example, methyl hydroxybenzoate.

Other preparations suitable for administration through the nose consist of a coarse powder displaying a particle size of 20 to 500 μm which is administered in the same way as snuff.

In addition to the ingredients mentioned above, the formulations according to the invention may contain one or more additional conventional and well-known components, such as, for example, dilution agents, buffer substances, flavourings, binding agents, surface active agents, thickening agents, lubricants, preservatives, antioxidants, emulsifiers and similar.

The following examples explain the invention without limiting it to the examples.

EXAMPLE 1 a) Isolation of androsin from plant material (Picrorhiza Kurroa Royle and Benth).

Picrorhiza Kurroa is a plant with tubular roots which grows in India.

The pulverized roots of Picrorhiza Kurroa are subjected to exhaustive Soxhlet extraction with solvents of increasing polarity, e.g. hexane—chloroform—ethyl acetate— methanol. The extracts are tested for their biological activity, e.g. influence on histamine release in leukocytes. The active fractions are subjected to gel filtration (e.g. Sephadex® LH-20-column 2.5×78.5 cm). Methanol is used as the elution medium. Fractions containing androsin are identified by their biological activity, test as described above, combined and evaporated to dryness (the methanol extract contains about 1.6% androsin.)

b) Alternatively, pulverized roots are subjected to Soxhlet extraction with hexane, then with methanol. The methanol fraction is separated again as described in a) and the active fractions are identified by their activity in a corresponding test procedure.

Androsin can be identified by means of thin-layer chromatography. Separation takes place on $SiO_2$-plates with a mobile phase consisting of chloroform/methanol, 8.5:1.5, and detection with vanillin-sulfuric acid reagent, with fractions containing androsin colouring orange-red after heating to 100° C.

c) Method for manufacturing an extract of plant material enriched with androsin.

The fractions containing androsin obtained according to a) or b) are subjected to RP chromatography (RP-18-Lobar column) with methanol/water as the mobile phase. Using 20% methanol, the active ingredients are eluted and identified by means of their biological activity.

The methods described above for isolating androsin or for manufacturing an extract enriched with androsin essentially embrace the exhaustive extraction of pulverized roots of Picrorhiza Kurroa either with solvents starting with hexane and proceeding to methanol corresponding to the eluetropic series, by Soxhlet extraction, percolation, maceration or by supercritical gases ($CO_2$, butane) and enrichment of the fraction containing androsin or separation of the fraction not containing androsin by methods of column chromatography known to the specialist (e.g. gel permeation method, RP chromatography) or by a liquid/liquid distribution method.

EXAMPLE 2

Manufacture of compounds of the general formula (I) by chemical synthesis.

18 mmol of 2.5% potassium hydroxide is added to a solution of 10 mmol of acetophenone (commercially available) of the general formula

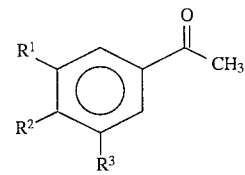

in which $R^1=CH_2O$ or H, $R^2=H$ or OH and $R^3=H$, OH, or $CH_3O$ in 10 to 15 ml of acetone, and stirred at room temperature for 10 min. Then a solution of β-acetobromglucose (14 to 16 mmol) is slowly added drop by drop to 20 to 30 ml of acetone and stirring continues for 24 to 40 hours. After neutralizing the reaction mixture with 10% hydrochloric acid and cooling to approx. 0° C., the precipitate is suctioned off or isolated after evaporation by means of extraction with methyl acetate. The recrystallisation of the product from methanol or ethanol yields the crystalline tetraacetylglucosyloxy acetophenone derivative with a yield of 20 to 40%.

1N sodium methylate (9 mmol) is added to a methanolic solution of 2 mmol of the compound obtained in the first step and stirred at room temperature for 2 to 3 hours. The reaction mixture is carefully neutralized with ion exchange resin (IR-120) and evaporated in a vacuum. The residue is recrystallized from water and yields the glucoside as a crystalline product with a yield of 60 to 70%.

For the production of the halogenated derivatives the acetophenone (0.01 mol) is dissolved in water or in a water-methanol mixture and is reacted after the addition of Na-acetate (1.5–3.0 g) with a solution of Na-hypochlorite (1.7 g) or K-iodide (0.5 g) and iodine (gaseous) or K-bromide and bromine (gaseous) at −60° C. to 90° C. for 1.5 to 3 hours (Cl, Br, I=0.01 mol). The reaction product is extracted with chloroform, washed with Na-thiosulfate and the crude product is recrystallisied from acetic acid. Thereafter the compound is used further as described above.

EXAMPLE 3

Biological Tests a) Inhibition of histamine release from human peripheral leukocytes by various solvent fractions of Picrorhiza Kurroa and androsin. Venous blood was withdrawn from atopic donors and the peripheral leukocytes were obtained by means of dextran sedimentation. The purified cells were preincubated with three or four different concentrations of the substance to be tested and with the solvent alone. After 10 minutes, rabbit antihuman IgE antibodies, plasma containing anaphylatoxin (C5a) according to Vallota and Müller-Eberhard, calcium ionophore or saline solution were added to the cells. 30 minutes later, the reaction was stopped and the histamine concentration was measured in the excess length by means of spectrofluorometry.

The results are shown in table 1 with the inhibition of the histamine release shown in percent of the maximal release by perchloric acid, corrected by the spontaneous release without stimulation.

b) Asthma-protective action of the acetophenone compound in guinea pigs.

Male white "Pirbright" guinea pigs were sensitized to ovalbumin by means of the well-known methods. Inhalation experiments were conducted 4 to 6 weeks later.

Spontaneously breathing animals were placed in a dual-chamber body plethysmograph in which the two chambers were separated around the head of the animals by a rubber collar filled with water. Changes in volume in the two chambers were measured by means of pressure transfer systems. The degree of bronchial obstruction was determined by means of the parameter, "compressed air". This technique is ten times more sensitive than other invasive methods (Dorsch et al., Pflügers Arch., 1981, 391: 236 to 241).

Groups of 10 to 14 animals were divided into two sub-groups and either treated with the test substance or with a solution. Three or four days later the experiments were repeated with those animals which had previously been given the control being given the test substance and vice-versa (each animal was once given either the test substance or the solvent).

Ovalbumin, histamine and acetylcholine were dissolved in saline solution; PAF was first dissolved in ethanol and then in saline solution containing 0.25% of bovine serum albumin to a final concentration of 1 µg PAF per ml. Ovalbumin, PAF, histamine and acetylcholine were administered in the form of an aerosol produced by ultrasound.

The effect of the test substance on the PAF-induced hyperreactivity was studied by means of successive inhalation of histamine, PAF and histamine. One group of animals was divided into two sub-groups with both sub-groups inhaling histamine in a dose leading to moderate bronchial obstruction. One hour later, one group was given the substance to be tested and the other group was given the solvent alone. Both groups were induced later by the successive inhalation of PAF and histamine. First 1 µg of PAF and 60 minutes later the same dose of histamine as before was given. The second contact with histamine in control animals usually leads to asthmatic reactions which are three times as great as after the first contact, The results of these experiments are shown in FIGS. 1 and 2.

As we can see from the figures, androsin given in an oral dose of 10 mg/kg body weight reduces PAF-induced bronchial asthma in vivo by 72% and allergic bronchial asthma by 67%. As an aerosol, androsin given in a dose of 0.5 mg/animal reduced PAF-induced reactions by 72% and allergic reactions by 67%. Essentially, the same effects are achieved with the compound, apocynin, and 2,4-dimethoxy-2-hydroxyacetophenone.

As we can see in table 1, the pure substance, androsin, was not effective in the in vitro experiment. However, the extracts containing androsin displayed a good inhibitory effect.

TABLE 1

| Fraction/compound | Concentration (mg/ml) | % Inhibition of histamine release | | |
|---|---|---|---|---|
| | | α-IgE | C5a | A 12387 |
| Chloroform frac. | 0.1 | 56.2 ± 45.2 | 8.9 ± 51.6 | 76.0 ± 13.8 |
| | 0.01 | 50.2 ± 28.8 | 1.7 ± 63.7 | 8.7 ± 12.9 |
| | 0.001 | 35.3 ± 30.6 | 6.4 ± 35.2 | 9.0 ± 7.5 |
| Ethyl acetate frac. | 0.1 | 64.4 ± 35.9 | 38.3 ± 42.5 | 62.9 ± 28.4 |
| | 0.01 | 48.2 ± 44.4 | 24.9 ± 30.0 | 6.5 ± 20.9 |
| | 0.001 | −3.0 ± 44.8 | 20.8 ± 23.8 | 1.8 ± 13.6 |
| Butanol frac. | 0.1 | 23.4 ± 59.4 | −13.9 ± 60.5 | 7.5 ± 41.6 |
| | 0.01 | 34.2 ± 52.9 | 13.3 ± 64.0 | −13.4 ± 29.7 |
| | 0.001 | 20.9 ± 56.7 | 32.1 ± 48.8 | −12.6 ± 18.1 |
| Water frac. | 0.1 | 42.9 ± 49.9 | −20.0 ± 22.3 | 7.1 ± 40.2 |
| | 0.01 | 33.8 ± 56.9 | −11.0 ± 37.4 | −9.7 ± 15.4 |
| | 0.001 | 48.9 ± 49.9 | −14.9 ± 45.9 | −4.3 ± 15.1 |
| Androsin | 0.1 | 10.9 ± 10.6 | −4.3 ± 26.7 | −12.5 ± 6.1 |
| | 0.01 | 5.5 ± 13.3 | 3.7 ± 16.3 | −14.9 ± 12.4 |
| | 0.001 | 0.5 ± 6.6 | −4.5 ± 28.2 | −0.4 ± 23.4 |
| | 0.0001 | 2.8 ± 9.0 | −5.4 ± 27.6 | −3.6 ± 23.3 |

We claim:

1. A method of prophylaxis and treatment of inflammatory diseases of the lung comprising inflammatory and/or allergic processes, asthma and obstructive bronchitis by administering an antiinflammatory preparation comprising at least one compound selected from the group of compounds having the formula:

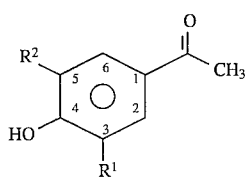

in which
R$^1$ and R$^2$ are each radicals independently selected from the group consisting of H, Cl, Br, I, methyl, hydroxy, methoxy, propoxy, isopropoxy and ethoxy, wherein R$^1$ and R$^2$ are not simultaneously H,
and the pharmaceutically acceptable salts, ethers and esters thereof and a pharmaceutically acceptable carrier therefor.

2. The method according to claim 1, wherein the inflammatory diseases comprise inflammatory processes of allergic pathogenesis.

3. The method according to claim 1, wherein R$^1$ denotes methyl and R$^2$ denotes H.

4. The method according to claim 1 in which R$^1$ denotes n-propoxy and R$^2$ denotes H.

5. The method according to claim 1 in which R$^1$ denotes isopropoxy and R$^2$ denotes H.

6. The method according to claim 1 in which R$^1$ denotes methoxy and R$^2$ denotes methoxy.

7. The method according to claim 1 wherein said inflammatory condition is selected from the group consisting of asthma and obstructive bronchitis.

8. A pharmaceutical formulation for the treatment of inflammatory diseases of the lung including inflammatory and/or allergic processes, asthma and obstructive bronchitis, the formulation comprising at least one compound selected from the group of compounds having the formula:

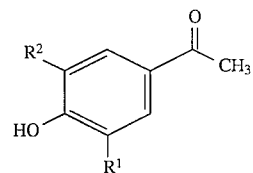

in which R$^1$ and R$^2$ are each radicals independently selected from the group consisting of H, Cl, Br, I, methyl, hydroxy, propoxy, isopropoxy and ethoxy, and the pharmaceutically acceptable salts, ethers and esters thereof, with the provision that R$^1$ and R$^2$ are not simultaneously H, in an effective treatment amount and a pharmaceutically acceptable carrier.

9. The pharmaceutical formulation according to claim 1 in which R$^1$ denotes methoxy and R$^2$ denotes methoxy.

* * * * *